United States Patent

Schmenger et al.

[11] Patent Number: 6,017,518
[45] Date of Patent: Jan. 25, 2000

[54] SILICONE-CONTAINING HAIR TREATMENT COMPOSITION

[75] Inventors: Jürgen Schmenger, Weiterstadt; Ernst Flemming, Heusenstamm; Bernd Stein, Hösbach, all of Germany

[73] Assignee: Wella Aktiengesellschaft, Darmstadt, Germany

[21] Appl. No.: 08/944,452

[22] Filed: Oct. 6, 1997

[30] Foreign Application Priority Data

Oct. 12, 1996 [DE] Germany ............ 196 42 227

[51] Int. Cl.$^7$ .................................................. A61K 7/06
[52] U.S. Cl. .................. 424/70.1; 424/70.12; 424/78.03
[58] Field of Search .............. 424/70.12, 70.11, 424/78.03

[56] References Cited

U.S. PATENT DOCUMENTS 5,089,243  2/1992  Halloran ..................................... 424/47
5,654,362  8/1997  Schulz ....................................... 524/862

FOREIGN PATENT DOCUMENTS

0452762A2  10/1991  European Pat. Off. .
359120664A  7/1984  Japan .

OTHER PUBLICATIONS

Chemical Abstract 112:164723v Hair Preparations Containing . . . Aug. 24, 1989.

Primary Examiner—Thurman K. Page
Assistant Examiner—William E. Benston, Jr.
Attorney, Agent, or Firm—Michael J. Striker

[57] ABSTRACT

The hair treatment composition includes (A) at least one polydimethylsiloxane with hydroxy end groups, advantageously α-hydroxy-ω-hydroxy-poly[oxy(dimethylsilylene)]; (B) at least one volatile, linear or cyclic polydimethylsiloxane, advantageously octamethylcyclotetrasiloxane, and (C) at least one isoparaffin, advantageously an isomeric mixture of isododecanes. Also the composition is advantageously free of water or contains no more than 5 % water and is free of cross-linking agents. The composition forms a smooth protective film on hair which is treated with it, with brilliant luster, without loading the hair.

11 Claims, No Drawings

SILICONE-CONTAINING HAIR TREATMENT COMPOSITION

BACKGROUND OF THE INVENTION

The present invention relates to a composition for treatment of hair, and, more particularly, for the care and protection of hair.

The physical, chemical and morphological properties of hair are negatively effected by a variety of different things. Thus hair is strongly stressed and damaged by frequent washing with deoiling surfactants, by climatic influences, such as moisture and temperature differences, or by intensive action of sunlight, or mechanical treatments, such as brushing, combing and rubbing, as well as by cosmetic treatments, such as repeated bleaching, permanent wave treatments and dyeing. The hair becomes brittle and loses its luster.

Compositions are already known which protect, care for and impart luster to the hair. These compositions have the disadvantage however that they simultaneously load or leave an oily or fatty film on the skin and hair or that, when they are based on aqueous solutions, the desired care, protective or luster effect is not maintained for long. A hair treatment composition is described in U.S. Pat. No. 5,089,253, which has a content of polydiorganosiloxane with hydroxy end groups, a cross-linking agent and a low molecular weight carrier. This compositions has, especially, disadvantages in regard to the loading of the hair connected with it.

SUMMARY OF THE INVENTION

It is an object of the present invention to provide a hair treatment composition which cares for, protects and imparts luster to the hair, without unpleasantly loading the hair.

According to the invention the above-described object is attained by a hair treatment composition comprising (A) at least one polydimethylsiloxane with hydroxy end groups, (B) at least one volatile, linear or cyclic polydimethylsiloxane, and (C) at least one isoparaffin;

wherein this composition is water-free or contains at maximum 5% water and is preferably free of cross-linking agents.

The hair treatment composition according to the invention contains preferably from 0.01 to 50 percent by weight of component (A), especially preferably from 0.1 to 20 percent by weight. Polydimethylsiloxanes with hydroxy end groups are known under the designation, α-hydroxy-ω-hydroxypoly[oxy-(dimethylsilylene)], or under the CTFA designation, dimethiconol, (CTFA International Cosmetic Ingredient Dictionary, USA, 1991). Suitable dimethiconols, e.g., dissolved in a cyclic or linear polydimethylsiloxane, are marketed by Dow Corning, U.S.A., under the trade name, Dow Corning Q2-1401 and Q2-1403, or by Goldschmidt AG, Essen, Germany, under the trademark Abil® OSW 12 and Abil® OSW 13.

The composition according to the invention preferably contains from 0.1 to 80 percent by weight of component (B), particularly preferably from 5 to 50 percent by weight. Linear and cyclic polydimethylsiloxanes are also known under the CTFA designation, dimethicones and/or cyclomethicones. For example, polydimethylsiloxanes with a viscosity of 0.1 to 20,000 $mm^2s^{-1}$, preferably with a viscosity of 0.5 to 500 $mm^2s^{-1}$ are suitable volatile, linear polydimethylsiloxanes, for example the commercial product, Dow Corning 200 Fluid and 225 Fluid of Dow Corning, U.S.A., or Abil® 5000 and Abil® 10000 of Goldschmidt, Germany, or Belsil® DMC of Wacker, Germany.

Cyclomethicones with 4 to 6 silicon atoms or their mixtures are for example suitable volatile, cyclic polydimethylsiloxanes, for example the commercial products, Dow Corning 244 Fluid and Dow Corning 245 Fluid of Dow Corning, USA, Abil® K4 of Goldschmidt, Germany, or GE Silicone SF 1202 and 1173 of GE Silicones, U.S.A.

The composition according to the invention contains the component (C) preferably in an amount of from 0.1 to 80 percent by weight, particularly preferably in an amount of from 5 to 50 percent by weight. Suitable isoparaffins are branched hydrocarbons with from 4 to 20, preferably from 6 to 12 carbon atoms, of their mixture, for example, isodecane, isododecane or the commercially available Solvent ID of BP, Great Britain.

The composition according to the invention contains a maximum of 5 percent by weight water or is water-free and can preferably contain from 0.1 to 99.9 percent by weight, preferably from 10 to 50 percent by weight alcohol. Especially lower alcohols having from 1 to 4 carbon atoms, e.g. ethanol and propanol, which are usually used for cosmetic purposes, are suitable as the alcohols.

The hair care composition according to the invention can additionally contain those cosmetic ingredients, which are usually conventionally used in hair care compositions, especially perfume oil in an amount of advantageously from 0.01 to 5 percent by weight; turbidity inducing agents, such as ethylene glycol distearate, in an amount of preferably from 0.01 to 5 percent by weight; wetting agents or emulsifiers from the classes of anionic, cationic, amphoteric or nonionic surface active substances without cleaning or detergent action, such as fatty alcohol sulfates, ethoxylated fatty alcohols, fatty acid alkanolamides, such as esters of hydrogenated castor oil fatty acids, in an amount of preferably from 0.1 to 30 percent by weight; further vegetable oils and extracts, moisturizing agents, dye compounds, light protecting agents, antioxidants, luster imparting agents and preservatives, in an amount of preferably from 0.01 to 10 percent by weight.

The compositions according to the invention can be in different forms according to the application involved, such as liquid-solid preparations or in aerosol preparations, as a foam or as a spray, and also as a non-aerosol preparation which can be used by means of a pump or as a "pump and spray".

If the composition according to the invention is in the form of an aerosol spray, it also contains from 15 to 85 percent by weight, preferably from 25 to 75 percent by weight of a propellant and is dispensed from a pressurized container. Lower alkane, such as n-butane, i-butane and propane or their mixtures with dimethyl ether and also pressurized gases, such as $N_2$, $N_2O$ and $CO_2$ and their mixtures, can be used as the propellant.

The composition according to the invention can also be present in the form of a non-aerosol spray sprayable with the help of a suitable mechanically operated spraying device. A "mechanical spraying device" means a device which sprays a liquid without the use of a propellant. Suitable mechanical spraying devices include a spray pump or an elastic container provided with a spray valve, in which the cosmetic composition according to the invention is filled under pressure thus causing the elastic container to stretch and/or expand. Subsequently the composition is dispensed continuously, because of contraction of the elastic container, when the spray valve is opened.

The "treatment of human head hair" means for the purposes of making a hair-do or hair style or for care of the hair.

When hair is treated with the composition according to the invention, a smooth protective film with brilliant luster is formed without loading the hair. The volatile silicone polymers and the volatile isoparaffins bring about a satisfactory feel and make the hair stylable and can be combed during the treatment. After a short setting or styling time these ingredients evaporate and a care and luster providing film remains on the hair.

The following examples illustrate the hair treatment composition according to the invention.

EXAMPLES

Example 1: Luster-imparting Spray with UV Protective Action
- 30.0 g polydimethylsiloxane (viscosity = 0.65 mm²s⁻¹)
- 6.0 g α-hydroxy-ω-hydroxypoly[oxy(dimethylsilylene)], 12 percent solution in cyclomethicone (Abil ® OSW 12 of Goldschmidt, Germany)
- 0.1 g p-methoxycinnamic acid-2-ethylhexylester
- 25.0 g isomeric mixture of isododecanes (Solvent ID of BP, Great Britain)
- 38.9 g isopropanol 100.0 g Example 2: Hair Protective Film for Protecting Against Drying out
- 45.0 g polydimethylsiloxane (viscosity = 5000 mm²s⁻¹)
- 10.0 g α-hydroxy-ω-hydroxypoly[oxy(dimethylsilylene)], 13 percent solution in cyclomethicone (Q2-1403 ® of Dow Corning, USA)
- 35.0 g isomeric mixture of isododecanes
- 10.0 g isopropanol 100.0 g Example 3: Perfumed Luster-imparting Spray
- 35.0 g octamethylcyclotetrasiloxane
- 4.0 g α-hydroxy-ω-hydroxypoly[oxy(dimethylsilylene)], 13 percent solution in cyclomethicone (Abil ® OSW 13 of Goldschmidt, Germany)
- 1.0 g perfume
- 25.0 g isomeric mixture of isododecanes
- 35.0 g ethanol 100.0 g Example 4: Hair Cutting Lotion
- 30.00 g decamethylcyclopentasiloxane
- 0.50 g α-hydroxy-ω-hydroxypoly[oxy(dimethylsilylene)], 12 percent solution in cyclomethicone
- 0.25 g hexadecyltrimethylammonium chloride, 50% aqueous solution in isopropanol/water = 2.3/1
- 0.10 g perfume
- 40.00 g isomeric mixture of isododecanes
- 29.15 g ethanol 100.0 g Unless otherwise stated, all percentages are percentages by weight.

The disclosure in German Patent Application 196 42 227.2 of Oct. 12, 1996 is incorporated here by reference. This German Patent Application describes the invention described hereinabove and claimed in the claims appended herein in below and provides the basis for a claim of priority for the instant invention under 35 U.S.C. 119.

While the invention has been illustrated and described as embodied in a silicone-containing hair treatment composition, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A hair treatment composition containing
   at least one first silicone ingredient selected from the group consisting of polydimethylsiloxanes with hydroxy end groups;
   octamethylcyclotetrasiloxane; and
   at least one isoparaffin; and
   containing no more than 5% water and no cross-linking agents.

2. A hair treatment composition containing
   α-hydroxy-ω-hydroxy-poly[oxy(dimethylsilylene)];
   at least one second silicone ingredient selected from the group consisting of volatile linear polydimethylsiloxanes and volatile cyclic polydimethylsiloxanes; and
   at least one isoparaffin; and
   containing no more than 5% water and no cross-linking agents.

3. A hair treatment composition containing
   at least one first silicone ingredient selected from the group consisting of polydimethylsiloxanes with hydroxy end groups;
   at least one second silicone ingredient selected from the group consisting of volatile linear polydimethylsiloxanes and volatile cyclic polydimethylsiloxanes; and
   an isomeric mixture of isododecanes; and
   containing no more than 5% water and no cross-linking agents.

4. A hair treatment composition containing no more than 5 percent by weight water and no cross-linking agents, said hair treatment composition consisting essentially of:
   at least one first silicone ingredient selected from the group consisting of polydimethylsiloxanes with hydroxy end groups;
   at least one second silicone ingredient selected from the group consisting of volatile linear polydimethylsiloxanes and volatile cyclic polydimethylsiloxanes;
   at least one isoparaffin; and
   an alcohol having from 1 to 4 carbon atoms.

5. A hair treatment composition containing no more than 5 percent by weight water and no cross-linking agents, said hair treatment composition consisting of:
   at least one first silicone ingredient selected from the group consisting of polydimethylsiloxanes with hydroxy end groups;
   at least one second silicone ingredient selected from the group consisting of volatile linear polydimethylsiloxanes and volatile cyclic polydimethylsiloxanes;
   at least one isoparaffin;
   an alcohol having from 1 to 4 carbon atoms; and
   at least one cosmetic ingredient selected from the group consisting of perfume oils, turbidity-inducing agents, wetting agents, emulsifiers, antioxidants, luster-imparting agents, preservatives, light protecting agents, moisturizing agents and vegetable oils.

6. The hair treatment composition as defined in claim 2 or 3, containing from 0.01 to 50 percent by weight of said at least one first silicone ingredient.

7. The hair treatment composition as defined in claim 1 or 3, containing from 0.1 to 80 percent by weight of said at least one second silicone ingredient.

8. The hair treatment composition as defined in claim 1 or 3, containing from 0.1 to 80 percent by weight of said at least one isoparaffin.

9. The hair treatment composition as defined in claim 1 or 3 wherein said at least one second silicone ingredient has a viscosity of from 0.1 to 20,000 $mm^2s^{-1}$.

10. The hair treatment composition as defined in claim 1, 2 or 3, and free of said water.

11. The hair treatment composition as defined in claim 1, 2 or 3, further comprising from 10 to 50 percent by weight of an alcohol having from 1 to 4 carbon atoms.

* * * * *